United States Patent [19]
Kallman

[11] Patent Number: 6,056,696
[45] Date of Patent: May 2, 2000

[54] FRUSTRATED TOTAL INTERNAL REFLECTION ACOUSTIC FIELD SENSOR

[75] Inventor: Jeffrey S. Kallman, Pleasanton, Calif.

[73] Assignee: The Regents of the University of California, Oakland, Calif.

[21] Appl. No.: 09/148,744

[22] Filed: Sep. 4, 1998

[51] Int. Cl.[7] ...................................................... A61B 8/00
[52] U.S. Cl. ............................ 600/459; 128/915; 73/656
[58] Field of Search ................................. 600/437, 448, 600/459, 561, 587; 73/655–656; 128/915

[56] References Cited

U.S. PATENT DOCUMENTS

| | | | |
|---|---|---|---|
| 3,602,577 | 8/1971 | Byram | 356/161 |
| 4,286,468 | 9/1981 | Altman | 73/655 |
| 5,785,663 | 7/1998 | Sarvazyan | 600/587 |

Primary Examiner—Francis J. Jaworski
Attorney, Agent, or Firm—L. E. Carnahan

[57] ABSTRACT

A frustrated total internal reflection acoustic field sensor which allows the acquisition of the acoustic field over an entire plane, all at once. The sensor finds use in acoustic holography and acoustic diffraction tomography. For example, the sensor may be produced by a transparent plate with transparent support members tall enough to support one or more flexible membranes at an appropriate height for frustrated total internal reflection to occur. An acoustic wave causes the membrane to deflect away from its quiescent position and thus changes the amount of light that tunnels through the gap formed by the support members and into the membrane, and so changes the amount of light reflected by the membrane. The sensor(s) is illuminated by a uniform tight field, and the reflection from the sensor yields acoustic wave amplitude and phase information which can be picked up electronically or otherwise.

31 Claims, 4 Drawing Sheets

FRUSTRATED TOTAL INTERNAL REFLECTION ACOUSTIC FIELD SENSOR

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to acoustic sensors, particularly to an acoustic sensor which can acquire entire acoustic field or acoustic interference patterns, and more particularly to a frustrated total internal reflection acoustic field sensor for use in applications such as ultrasonic transmission tomography.

Ultrasound is used in a number of medical imaging and nondestructive testing modalities. Its advantages include a lack of ionizing radiation and good propagation through dense materials.

A pair of ultrasound modalities that have not been extensively utilized for medical imaging are: (1) acoustic diffraction tomography and (2) acoustic holography. A problem these modalities encounter are due to the lack of a fast way to acquire acoustic fields or acoustic interference patterns.

Due to the radiation risks of x-ray mammography, other approaches for breast cancer screening are being considered. Mammography is currently used for screening women over the age of 40 for breast cancer. It has not been used routinely on younger women because their breast composition is mostly glandular, or radio dense, meaning there is an increased radiation exposure risk as well as a high likelihood of poor image quality. For these younger women, it is calculated that the radiation exposure risk is higher than the potential benefit from the screening. It is anticipated that transmission ultrasound will enable screening of much younger women and complement mammographic screening in women 40 and over.

Ultrasonic transmission tomography holds out the hope of being a discriminatory tool for breast cancer screening that is safe, comfortable, and inexpensive. From its inception, however, this imaging modality has been plagued by the problem of how to quickly and inexpensively obtain the data necessary for the tomographic reconstruction.

Frustrated total internal reflection provides a way to acquire this data. Total internal reflection occurs when light approaches a dielectric interface at or above the critical angle. If there is another interface a short distance away, some light tunnels through the gap between the interfaces, which frustrates the total internal reflection. The amount of light that tunnels is strongly dependent on the size of the gap.

The present invention involves an acoustic field sensor utilizing frustrated internal reflection, which allows the acquisition of the acoustic field over an entire plane all at once and thus solves the prior problems relative to acoustic holography and acoustic diffraction tomography. When an array of sensors, made in accordance with the present invention, is illuminated by a uniform light field, the reflection from the array yields acoustic wave amplitude and phase information which can be picked up electronically or otherwise.

SUMMARY OF THE INVENTION

It is an object of the present invention to provide an acoustic sensor.

A further object of the invention is to provide a frustrated total internal reflection acoustic field sensor.

Another object of the invention is to provide an acoustic field sensor which allows the acquisition of the acoustic field over an entire plane all at once.

Another object of the invention is to provide a frustrated total internal reflection acoustic field sensor for use in acoustic nondestructive evaluation, acoustic holography, acoustic tomography, medical imaging, or other acoustic imaging techniques.

Another object of the invention is to provide a frustrated total internal reflection acoustic field sensor having increased sensitivity and frequence response, while reducing crosstalk and fabrication difficulties.

Another object of the invention is to provide an array of frustrated total internal reflection acoustic field sensors illuminated by a uniform light field for yielding acoustic wave amplitude and phase information which can be picked up electronically or otherwise.

Other objects and advantages of the present invention will become apparent from the following description and accompanying drawings. The heart of the ultrasound sensor of this invention is the conversion of sound pressure to optical modulation. The transformation from sound to light comes about because the sound energy changes the gap between a membrane and an optical substrate. The substrate is illuminated in such a way that the light is subject to total internal reflection. The membrane frustrates this reflection in a manner that is extremely dependent on the gap between membrane and substrate and thus modulates the light reflecting off the gap by an amount dependent on the acoustic pressure on the membrane. This modulated beam can be recorded by an optical sensor, and the phase and amplitude of the acoustic waveform can be extracted as a function of position on the plane. Each plane of data constitutes a projection. A three-dimensional reconstruction of the object can be generated by combining a series of these projections.

Basically, the present invention is a frustrated total internal reflection acoustic field sensor. The sensor solves the prior problems relative to the use of acoustic diffraction tomography and acoustic holography for medical imaging by providing a fast way to acquire entire acoustic fields or acoustic interference patterns. An array of sensors made in accordance with the present invention yields acoustic wave amplitudes and phase information which can be utilized in a variety of applications. The invention provides a sensor for applications such as acoustic nondestructive evaluation, acoustic holography and tomography, and other acoustic imaging techniques. The sensor of the invention utilizes two spaced interfaces forming a gap therebetween, one interface comprising a flexible membrane and which may be index matched to the other interface (a transparent support plate). An acoustic wave causes the membrane to deflect away from its quiescent position and thus changes the amount of light that tunnels through the gap and into the membrane, thus changing the amount of light reflected by the substrate.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

The invention is directed to a frustrated total internal reflection acoustic field sensor. The acoustic field sensor of this invention allows the acquisition of an entire acoustic field at one time. The sensor of this invention provides a fast way to acquire acoustic fields or acoustic interference pattern and thus enables the use of acoustic diffraction tomography and acoustic holograph for medical imaging, such as ultrasonic transmission tomography for breast cancer screening. There are many other applications for the frustrated total internal reflection acoustic field sensors of this invention, which include acoustic nondestructive evaluation, acoustic holography, acoustic tomography, or other acoustic imaging techniques.

Since ultrasound does not travel well in air the sensor must be exposed to a liquid (such as water). In the following description, although not shown except in FIG. 4, it is to be understood that the membrane is exposed to a liquid on the side away from the optical substrate.

The basic physical principle used in the ultrasonic sensing of the present invention is frustrated total internal reflection (a consequence of optical refraction). Refraction occurs when a wave crosses an interface between media in which the speeds of light are different (i.e., of different refractive indices). If light moves from a slow medium to a fast medium, there is a critical angle beyond which the wave is reflected from the interface (with the exception of an evanescent wave that extends into the fast medium).

Frustrated total internal reflection occurs when another slow medium intercepts the evanescent wave. Some light tunnels though the gap (formed between the two slow media) and propagates into that medium. The amount of light that tunnels is directly related to the gap width.

Figure 1:
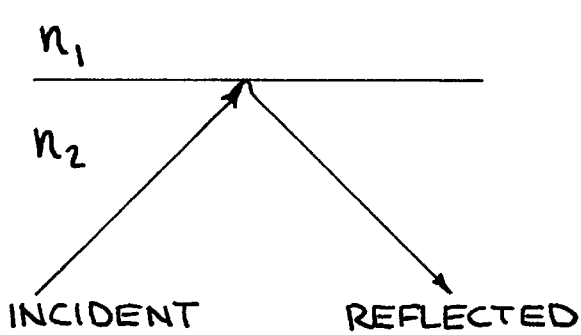
FIG. 1 graphically illustrates total internal reflection.
Figure 2:
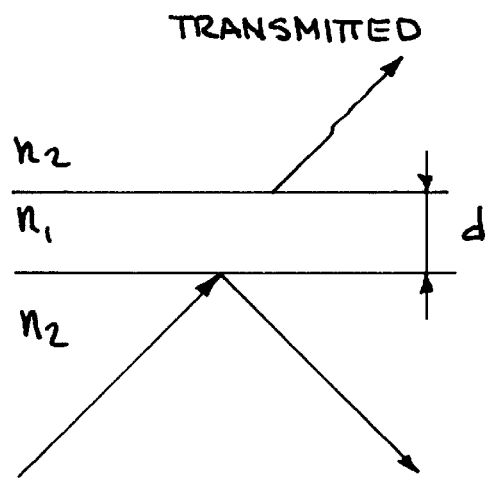
FIG. 2 graphically illustrates frustrated total internal reflection.
Figure 3:
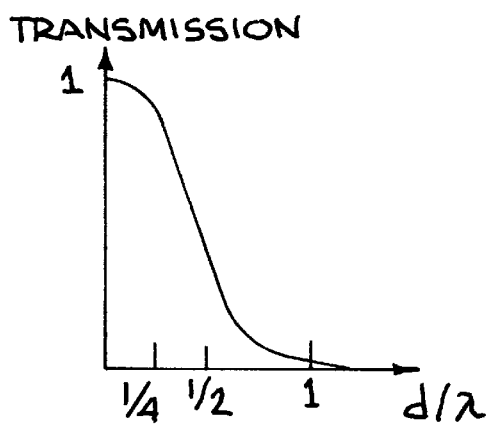
FIG. 3 graphically illustrates transmission vs. gap width (d) as shown in FIG. 2.

Frustrated total internal reflection gives a way to acquire data relative to acoustic fields or acoustic interference patterns. As pointed out above, total internal reflection (TIR) occurs when light approaches a dielectric interface between an optically slow medium (n2) and a fast medium (n1), at or above the critical angle, as illustrated in FIG. 1. Frustrated TIR occurs when another slow medium intercepts the evanescent wave, such as when there is another interface a short distance away of another slow medium (n2), whereby a gap is formed and some light tunnels through the gap between the interfaces, frustrating the TIR, as shown in FIG. 2. The amount of light that tunnels is strongly dependent on the size or width of the gap. FIG. 3 graphically illustrates the transmission vs. gap size, the gap size being shown in wavelength. As pointed out above the sensor of this invention is constructed such that one side of the membrane is exposed to a liquid.

An array of frustrated total internal reflectors may be produced, for example, by creating a transparent plate with spaced support lines or walls secured to the plate which are tall enough to support a flexible membrane at an appropriate height for frustrated total interest reflection to occur. The spacing between the support lines or walls is such that there are at least three support lines per the shortest acoustic wavelength of interest (need at least two membrane resonators per acoustic wavelength). The membrane is flexible, may be index matched to the plate, may be optically absorbing, and is exposed to the liquid ultrasound medium on the side away from the optical substrate. An acoustic wave causes the membrane to deflect away from its quiescent position and thus changes the amount of light that tunnels through the gap and membrane into the ultrasound medium, and so changes the amount of light reflected. The array of sensors is illuminated by a uniform light field, and the reflection from the array yields acoustic wave amplitude and phase information which can be picked up electronically or otherwise.

Figure 4:
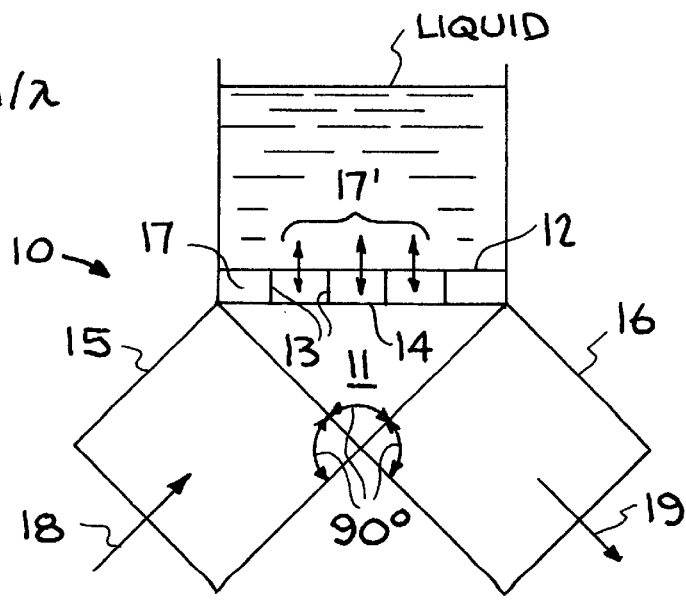
FIG. 4 is a side view of an embodiment of an acoustic field sensor made in accordance with the present invention.

FIG. 4 schematically illustrates a side view of an embodiment of an acoustic field sensor based on frustrated total internal reflection in accordance with the present invention. As shown, the sensor of FIG. 4, generally indicated at 10, basically includes a substrate or plate 11, a flexible membrane 12, and a plurality of support lines or walls 13. The substrate or plate 11 may be constructed of suitable transparent material, such as glass, plastic or silicon, and includes a flat central section 14 and side sections 15 and 16 which form three 90° angles at a point opposite flat section 14. The flexible membrane 12 is constructed of material that may be optically absorbing or may be index matched to the plate or substrate 11, and may, for example, be constructed of silicon nitride, silicon or glass (depending on optical wavelength) with a thickness of 0.1 $\mu$m to 1 $\mu$m. Lines or walls 13 support membrane 12 and form a gap 17 between the flexible membrane 12 and the plate or substrate 11, and are spaced such that there are at least three support lines per the shortest acoustic wavelength of interest, which may, for example, range from 0.1 mm to 5.0 mm. For example, the support lines or walls 13 may be constructed of silicon or an easily deposited metal (gold, aluminum, chromium), and may be non-transparent or transparent. The lines or walls, for example, may constitute metal lines bonded to the plate or substrate and be about ¼ micron thick and 1.0 to 10 microns wide.

In operation of the embodiment of FIG. 4, the membrane 12, which is flexible, may be index matched to the plate or substrate 11, and immersed in fluid, is subjected to an acoustic wave which causes the membrane 12 to deflect away from its quiescent position (upward or downward with respect to the flat central section 14 of substrate or plate 11) as indicated by the arrows 17' and thus changes the amount of light that tunnels through the gap 17 and through the membrane, and so changes the amount of light reflected, as described above with respect to FIG. 2. The membrane 12 may or may not be optically absorbing. The array of sensors of FIG. 4 is illuminated by a uniform light field, as indicated at 18, and the reflection from the array yields acoustic wave amplitude and phase information, indicated in FIG. 4 by arrow 19, which can be picked up electronically or otherwise.

Figure 5:
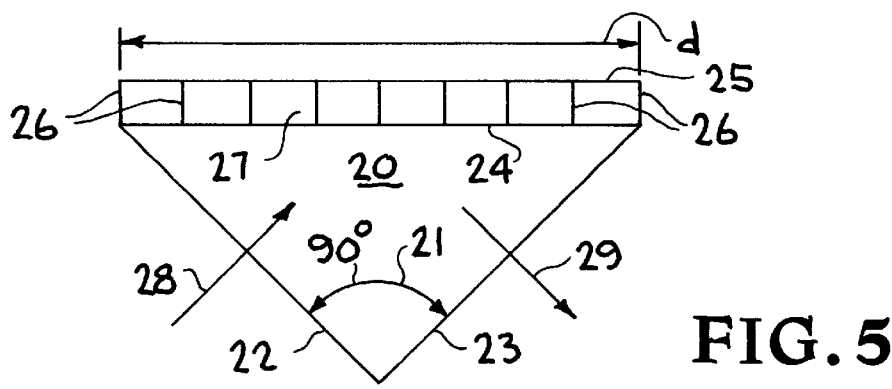
FIGS. 5, 6 and 7 schematically illustrate various embodiments of acoustic field sensors made in accordance with the present invention.
Figure 6:
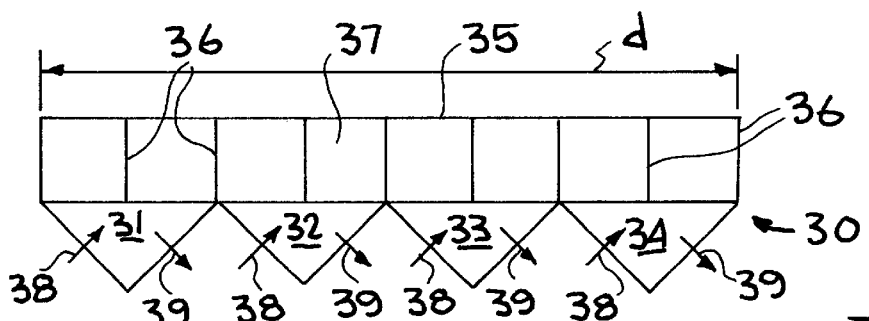
Figure 7:
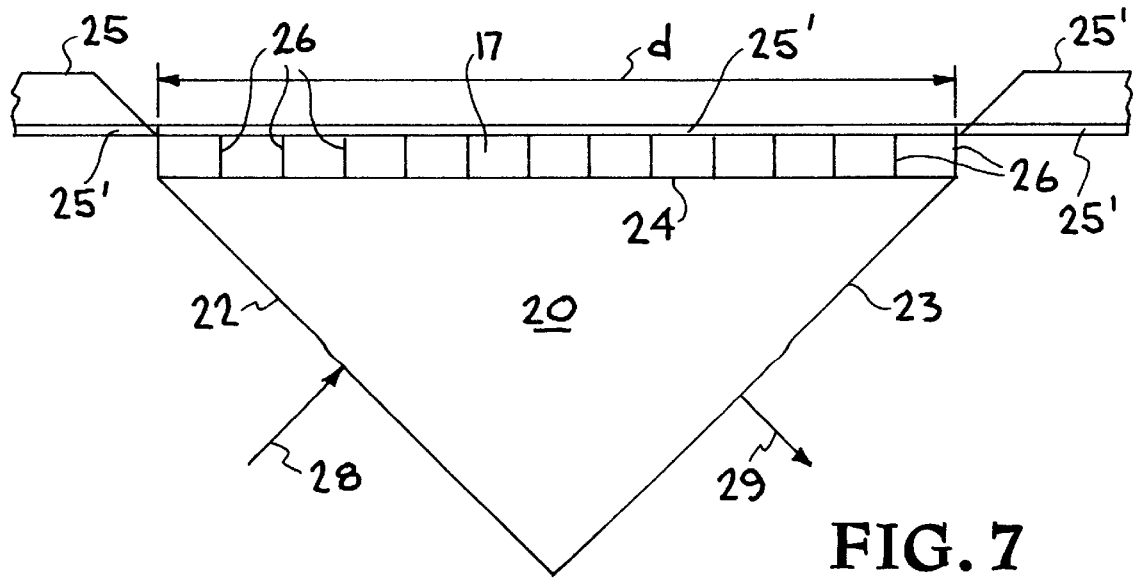

FIGS. 5–7 illustrate embodiments of the sensor which utilize a substrate with an inverted triangular shaped cross-section on which the membrane or membranes are mounted.

The transparent substrate 20 is configured to include a 90° angle indicated at 21, which intersects sides 22 and 23, with a side 24 being located opposite angle 21. One or more flexible membranes 25 are mounted in spaced relation to side 24 of substrate 20 by a plurality of support lines or walls 26, made of material, such as gold, to form a gap 27, which, for example, may be of a distance of one quarter wavelength from substrate side 24. Pulsed light from a source, not shown, is directed into substrate 20, as indicated by arrow 28, and data from the sensor is discharged from the substrate, as indicated by arrow 29. Sensors using single substrates are most effective for relatively small sensors, wherein the distance (d) across the membrane(s) is up to about 1.5 cm.

Where applications require larger sensors, up to four (4) inches, for example, the single substrate approach is ineffective. FIG. 6 illustrates an embodiment capable of operations requiring membrane(s) distances (d) of four inches. In this embodiment, a transparent substrate 30 having four triangular shaped sections 31, 32, 33, and 34 is utilized to support membranes 35 via support lines or walls 36 forming a gap 37, whereby pulsed light from a source, not shown, is directed into each of sections 31–34, as indicated by arrows 38, and data is extracted from each of the substrate sections, as indicated by arrows 39, which data are then collected and combined for use as described.

FIG. 7 illustrates an embodiment similar to FIG. 5, except that the membrane(s) are formed in a member having a layer of silicon nitride deposited on one surface and by removing a section of the member, so as to leave only the silicon nitride layer. Corresponding components are given like reference numerals. Here, a member 25, constructed of material such as silicon, is provided with a layer 25', such as silicon nitride, and the material of member 25 is removed along a distance (d) whereby only the silicon nitride layer 25' remains to form a membrane. By use of this arrangement, a variety of membranes or layers 25' of different distances (d) may be formed in a single member 25, which member serves as a support frame for the membranes.

Figure 8:
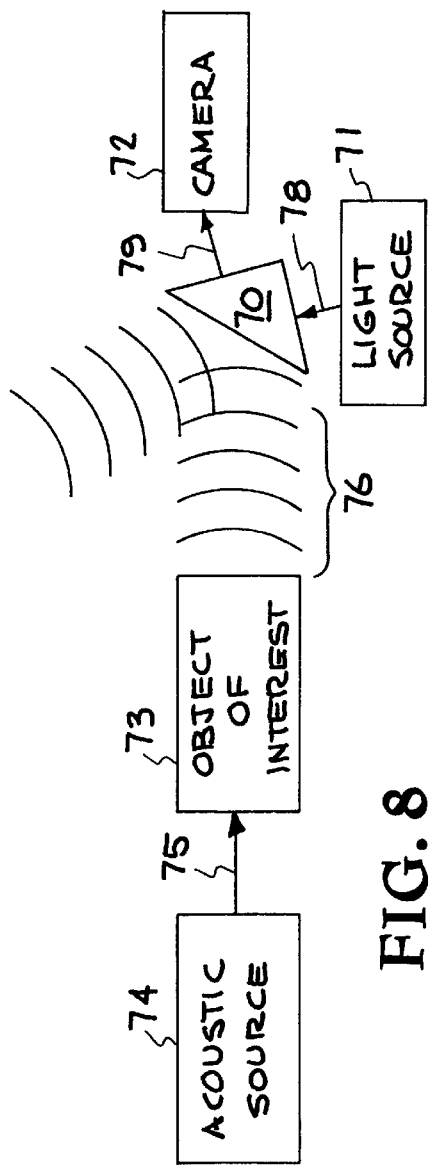
FIGS. 8 and 9 illustrate ways to get phase and amplitude using an acoustic field sensor.
Figure 9:
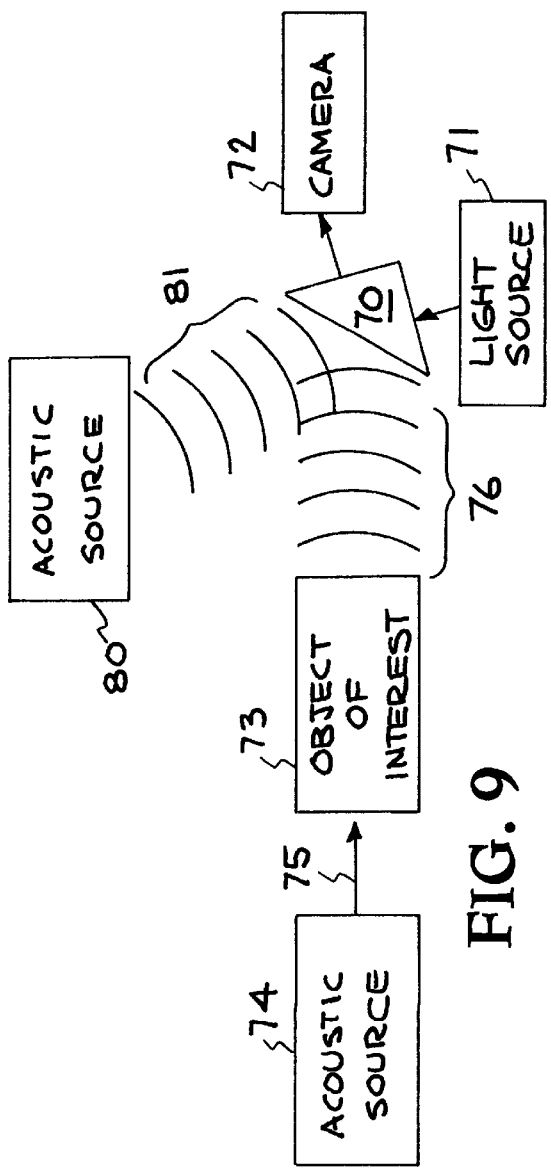

There are three ways to get the desired phase and amplitude of the acoustic field sensors of the present invention. The first and easiest is to utilize a strobed (pulsed) light source and an open camera shutter. The second and harder is to utilize a constant light source and a shuttered (fast) camera. The third and most difficult is to form an acoustic hologram. FIG. 8 illustrates schematically a system for carrying out the first and second approach described above, the only difference being that the light source for the first approach is pulsed, while the light source for the second approach is constant; and that for the first approach the camera shutter is opened and for the second approach it is fast shuttered. FIG. 9 illustrates schematically a system for carrying out the third approach described above. In this system an additional acoustic source is utilized which directs acoustic signals directly onto the sensor, and the light source is constant with a non-shuttered camera.

Referring now to the systems of FIGS. 8 and 9, similar components will be given similar reference numerals. The system, as shown in FIG. 8, includes a sensor 70, such as illustrated in FIGS. 4–7 and 10–11, a light source 71, which may be either pulsed or constant, and a camera 72, which may be a vidicon, a complimentary metal on silicon (CMOS), or a charge coupled device (CCD) camera, for example, an object of interest 73 such as a human breast, and an acoustic source 74, which directs acoustic energy as indicated by arrow 75 onto object 73, which produces signals or waves 76, which strike sensor 70, with a portion of the signals 76 being reflected as indicated at 77. The sensor 70, light source 71, and camera 72 function as described above, wherein the light source 71 illuminates the substrate of the sensor 70, as indicated by arrow 78, and data from the substrate of sensor 70 is directed onto camera 72, as indicated by arrow 79.

The FIG. 9 system additionally includes a second acoustic source 80, which directs energy waves 81 onto sensor 70, which results in an acoustic interference pattern on the sensor 70. In this system the light source 71 is of a constant type. In each of the systems of FIG. 8 and 9, the sensors 70 are positioned at an angle with respect to horizontal to minimize the reflection of acoustic energy backs to their sources.

Figure 11:
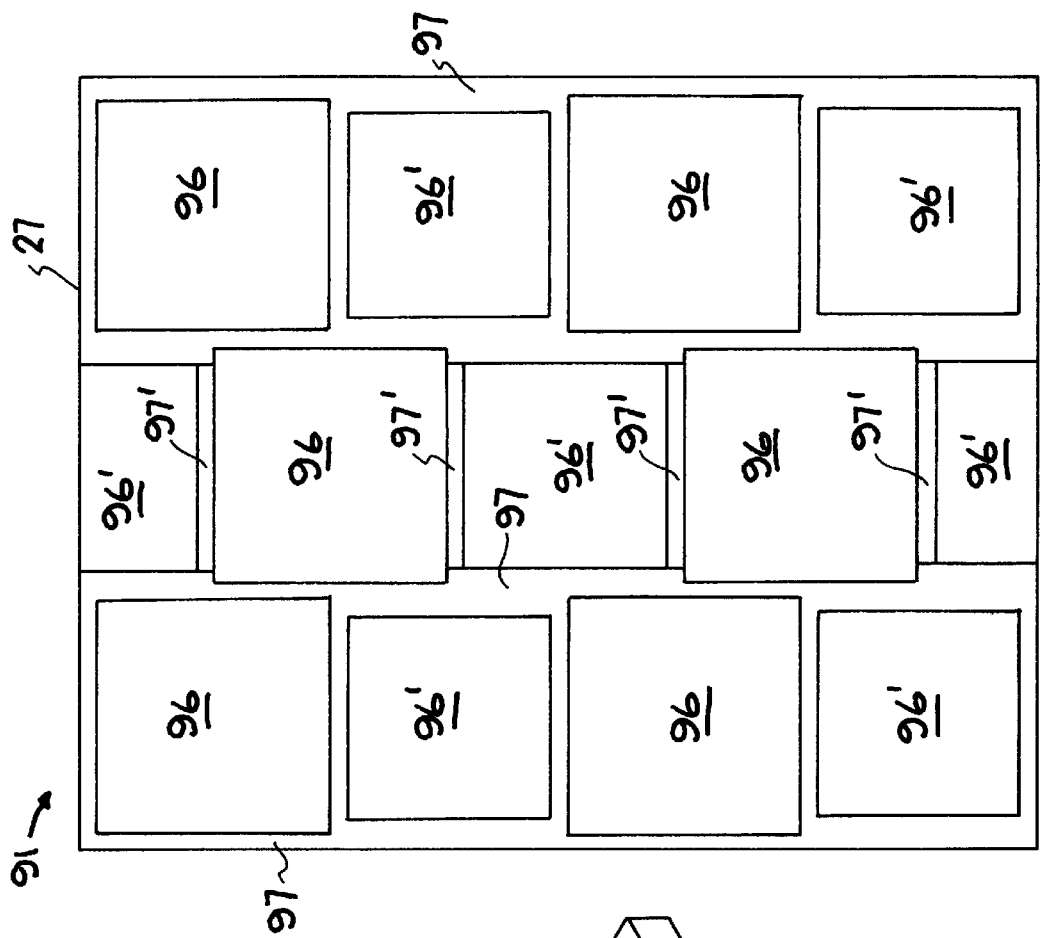
FIG. 11 is a view and a support frame of another embodiment illustrating the support lines or members, with the membrane being located beneath the frame which gives a mosaic appearance on the underside of the membrane (an upside-down view of one membrane).
Figure 10:
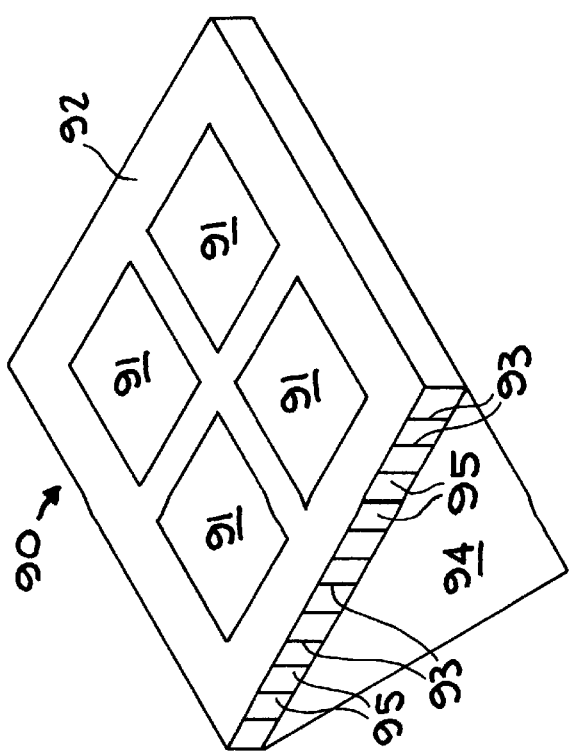
FIG. 10 is a perspective view of another embodiment of the sensor using a mosaic of membranes held in a frame and supported in spaced relation to a substrate.

In an effort to further optimize parameters and also eliminate perceived problems, such as increased sensitivity and frequence response while reducing crosstalk and fabrication difficulties, the embodiments of FIGS. 10 and 11 have been developed.

The FIG. 10 embodiment of the sensor of the present invention, generally indicated at 90, is composed of a mosaic of 1 cm by 1 cm by 0.1 micron silicon nitride membranes 91 held in a frame or support 92 of silicon, supported by metal members or lines 93 approximately 0.25 microns thick (height) and for example, 1.0 to 10.0 microns wide, and which are bonded to a transparent (glass) substrate 94 to form a plurality of gaps 95 between substrate 94 and frame 92. With the membranes 91 made of silicon nitride, for example, the metal support lines or members 93 may be made of aluminum, gold, or chromium, for example. While the membranes 91 are shown as square they may be rectangular or other appropriate configurations. The sensors, such as 90 in FIG. 10, may be mounted vertically (hanging) or be positioned horizontally, or at an angle, depending on the application.

FIG. 11 illustrates a membrane arrangement of FIG. 10 where the membranes 91 of FIG. 10 may be mounted on a frame such that from a bottom view each appears to be membrane 91 composed of staggered submembranes 96 and 96' with metal line partitions 97 and 97' between the submembranes, when in fact the submembranes 96 and 96' are exposed sections of membrane 91 located beneath the frame or metal line partitions 97-97'. For example, each of the submembranes 96 may be approximately 40 microns by 40 microns square with submembranes 96' being smaller, but can be of other appropriate configurations. As seen in FIG. 11, every other submembrane 96' is of a smaller dimension than that of other submembranes 96, and every column of submembranes is staggered relative to its adjacent columns. At these exemplified dimensions, the submembranes 96-96' are small enough to resonate at approximately 1 MHz (~1.5 mm wavelength in water), yet large enough to not have optical diffraction significantly affect their operation. In addition, the resonant structure is sensitive enough that human-safe acoustic power levels (<720 mW/cm$^2$) will cause easily seen changes in the optical response. The submembranes (96-96') are staggered and only approximately 40×40 microns square [some slightly larger (96), some slightly smaller (96')] in order to combat crosstalk. For example, with the submembranes 96 being 40×40 microns, the submembranes 96' may be 36–38×36–38 microns. If the submembranes (96-96') are either not staggered or are all the same size, crosstalk significantly impacts sensitivity and resolution.

The frustrated total reflection effect is being used to build a sensor for ultrasound, converting acoustic energy into optical modulation (which can be acquired over an entire two-dimensional plane at a time). The device will consist of a 2-D array of approximately 1,000,000 individual sensors. Each sensor will consist of a membrane mounted on walls less than half of an acoustic wavelength apart at a height of a quarter of an optical wavelength above a substrate surface. When the acoustic pressure pattern is imposed on the membrane it will deflect. The deflection will depend on the spatial distribution and intensity of the acoustic energy. As the membrane moves, the amount of light tunneling through it will vary. A uniform field of light illuminating the entire sensor array at the critical angle will have the acoustic pressure field imposed upon its reflection. The resultant optical data will be captured by a CCD camera. By strobing the light source and collecting a sequence of images, acoustic amplitude and phase information over an entire plane can be collected.

These data are precisely what are necessary for reconstructing the internal sound speed and attenuation of an object being probed by ultrasound. There are any number of algorithms available to perform this inversion, but diffraction tomography is currently a preferred approach.

Many factors determine the sensitivity of this acoustic sensor. Among these are the size of the individual acoustic pixels, the stiffness of the membrane, the wavelength of light used, and the optical source and sensor.

Simulations thus far show that an ultrasonic sensor will be sensitive enough that an acoustic power of 3 mW/cm$^2$ will cause detectable optical modulation (for a 40 $\mu$m sensor, there will be approximately a 5 percent modulation in the optical signal when excited at resonance with a power of 3 mW/cm$^2$). This is well within the safe limits for human tissue.

It has thus been shown that the present invention provides a frustrated total internal reflection acoustic field sensor which allows the acquisition of an entire acoustic field all at once, and enables acoustic holography and acoustic tomography to be utilized for medical imaging. Thus the acoustic field sensor of the present invention makes a substantial contribution to the field of acoustic imaging.

While the acoustic field sensor of this invention has numerous applications, it is particularly applicable for use in ultrasonic transmission tomography, as a replacement for x-ray mammography, and uses no ionizing radiation, requires no breast compression, consumes no resources, and generates no toxic waste, and thus will be discriminating, safe, comfortable, and inexpensive.

The data derived by the imaging system will be a 3-D volumetric representation of acoustic speed and attenuation in the breast. These data, in concert with computer pattern recognition techniques and human diagnostic skill, will make possible differentiation between types of tissues and the earlier detection of tumors.

Imaging without ionizing radiation allows the new screening technique to eliminate the tradeoff between early detection and radiation dose. Women of any age can be screened at any frequency without fear of inducing a tumor. This, in conjunction with the discriminatory power of the imaging technique, will bring abnormalities to light earlier than would otherwise be possible.

The pain of compression in conventional x-ray mammography is another factor that inhibits many women from undergoing breast cancer screening. Compression is not required in the transmission ultrasound imaging modality. For ultrasonography, the breast will be immersed in a body-temperature gel that matches the acoustic index of the breast. Comfort will increase compliance for women of all ages, reducing the risk from interval cancers that form between screenings. The ultrasound imaging modality will also improve detection of tumors in younger women who have glandular tissue that can't be imaged with x-ray mammography.

While particular embodiments, materials, parameters, etc., have been described and/or illustrated to exemplify and teach the principles of the invention, such are not intended to be limiting. Modifications and changes may become apparent to those skilled in the art, and it is intended that the invention be limited only by the scope of the appended claims.

The invention claimed is:

1. A frustrated total internal reflection acoustic field sensor, comprising,
    a transparent substrate,
    a plurality of spaced support members mounted on said transparent substrate and spaced such that there are at least three walls per the shortest acoustic wavelength of interest, and
    at least one flexible membrane supported by said support members such that a gap is formed between said transparent substrate and said at least one flexible membrane.

2. A frustrated total internal reflection acoustic field sensor, comprising,
    a transparent substrate,
    a plurality of spaced support members mounted on said transparent substrate, and
    at least one flexible membrane supported by said support members such that a gap is formed between said transparent substrate and said at least one flexible membrane,
    said at least one flexible membrane being configured as a mosaic composed of a plurality of flexible membranes.

3. The sensor of claim 2, wherein said plurality of flexible membranes of said mosaic each have dimensions of about 1 cm by about 1 cm by about 0.1 micron.

4. The sensor of claim 3, wherein said plurality of flexible membranes are retained in a frame supported by said support members, and wherein said support members define a plurality of metal lines bonded to said transparent substrate.

5. The sensor of claim 4, wherein said metal lines are about 0.25 microns thick and about one to 10 microns wide.

6. The sensor of claim 5, wherein said flexible membranes are constructed of silicon nitride, wherein said metal lines are constructed of gold, wherein said transparent substrate is constructed of glass, and wherein said frame is constructed of silicon.

7. The sensor of claim 2, wherein at least one of said plurality of flexible membranes is composed of a plurality of flexible submembranes, and wherein said support members ire positioned to support said submembranes.

8. The sensor of claim 7, wherein said plurality of flexible submembranes are positioned in a staggered arrangement.

9. The sensor of claim 7, wherein each of said flexible submembranes are of a different size than the submembranes adjacent thereto.

10. The sensor of claim 7, wherein each of said submembranes is approximately 40 microns square and has a thickness of about 0.1 microns.

11. The sensor of claim 7, wherein each of said submembranes is about 36–40 microns by 36–40 microns, with a thickness in the range of 0.1 to 1.0 microns.

12. The sensor of claim 7, wherein said support members comprise a plurality of metal lines approximately ¼ micron thick and at least 2.0 microns wide, said metal lines being secured to said transparent plate.

13. The sensor of claim 1, wherein said transparent substrate is constructed of material selected from the group consisting of glass, silicon, and plastic; wherein said flexible membranes are constructed of material selected from the group consisting of silicon nitride, silicon, and glass; and wherein said support members are constructed of material selected from the group of aluminum, gold, chromium, and silicon.

14. The sensor of claim 1, wherein said plurality of spaced support members are of an appropriate height to enable frustrated total internal reflection to occur in said gap.

15. The sensor of claim 1, wherein the acoustic wavelength of interest is in the range of 0.1 mm to 5 mm.

16. The sensor of claim 1, wherein said transparent substrate is of a triangular configuration.

17. The sensor of claim 1, wherein said transparent substrate is composed of a plurality of triangular shaped sections.

18. The sensor of claim 1, wherein said at least one membrane is defined by a thin section of a transparent member.

19. The sensor of claim 1, wherein said at least one flexible membrane is selected from the group consisting of optically absorbing membranes, index matched membranes, and membranes which are neither or either optically absorbing and index matched to the substrate.

20. An array of frustrated total internal reflectors comprising:

a transparent substrate with support members tall enough to support at least one flexible membrane at an appropriate height for frustrated total internal reflection to occur, said support members having a spacing therebetween which is such that there are at least three support members per the shortest acoustic wavelength of interest, said at least one flexible membrane being selected from the group consisting of membranes index matched to said substrate, optically absorbing membranes, and membranes that are neither index match or optically absorbing, whereby upon said array being illuminated by a uniform light field, and an acoustic wave causes the flexible membrane to deflect away from its quiescent position causing a change in the amount of light that tunnels through the gap between the substrate and flexible membrane and thus changes the amount of light reflected by the substrate, the reflection from the array yields acoustic wave amplitude and phase information.

21. The array of claim 20, wherein said at least one flexible membrane is configured as a mosaic having a plurality of flexible membranes.

22. The array of claim 21, wherein said plurality of flexible membranes are positioned in a support frame, said support frame being positioned on said support members.

23. The array of claim 22, wherein said support members are constructed in the configuration of spaced lines secured to said substrate.

24. The array of claim 20, wherein at least one of said plurality of flexible membranes is composed of a plurality of flexible submembranes, said plurality of flexible membranes being configured from the group consisting of staggered submembranes and submembranes of at least two different sizes.

25. The array of claim 24, wherein said support members are figured as lines secured to said substrate and which provide support about the periphery of said plurality of flexible submembranes.

26. The array of claim 20, wherein said transparent substrate is composed of glass; wherein said support members are composed of lines of material selected from the group consisting of aluminum, gold, chromium and silicon; wherein said it least one flexible member is composed of silicon nitride.

27. The array of claim 20, wherein said transparent substrate is composed of material selected from the group consisting of glass, silicon and plastic; wherein said support members are composed of material selected from the group of metal, silicon, plastics, and ceramics; and wherein said at least one flexible membrane is composed of material selected from the group consisting of silicon nitride, silicon and glass.

28. The array of claim 20, wherein said at least one flexible membrane has a thickness of about 0.1 microns and having sides of a length in the range of about 40 microns to about 2 centimeters, and wherein said support members comprise support lines of about ¼ micron thick and about 1.0 to 10.0 microns wide.

29. In a system for screening breast cancer, the improvement comprising:

a frustrated total internal reflection acoustic field sensor, a light source for illuminating said sensor, an acoustic source as for producing waves which are directed onto said sensor, and means for receiving, data from said sensor.

30. The improvement of claim 29, wherein said light source is selected from the group consisting of pulsed light and constant light.

31. The improvement of claim 29, additionally including a second acoustic source directing waves onto said sensor.

* * * * *